US010653197B2

(12) United States Patent
Perusse et al.

(10) Patent No.: US 10,653,197 B2
(45) Date of Patent: May 19, 2020

(54) HARD HAT WITH FILTERED, BATTERY-OPERATED AIR FLOW SYSTEM AND METHOD

(71) Applicant: Poma 22 LLC, Mendota Heights, MN (US)

(72) Inventors: Steve H. Perusse, Mendota Heights, MN (US); Steve Harrington, Carlsbad, CA (US); Joy Salvatin Lee, Carlsbad, CA (US); Carl Tedesco, Carlsbad, CA (US); Marc McCauley, Elk River, MN (US)

(73) Assignee: POMA 22, LLC, Mendota Heights, MN (US)

( * ) Notice: Subject to any disclaimer, the term of this patent is extended or adjusted under 35 U.S.C. 154(b) by 105 days.

(21) Appl. No.: 15/933,925

(22) Filed: Mar. 23, 2018

(65) Prior Publication Data

US 2019/0289946 A1 Sep. 26, 2019

(51) Int. Cl.
| | | |
|---|---|---|
| *A42B 1/00* | (2006.01) | |
| *A62B 18/00* | (2006.01) | |
| *A42B 3/28* | (2006.01) | |
| *A61M 16/10* | (2006.01) | |
| *A62B 18/04* | (2006.01) | |

(52) U.S. Cl.
CPC .............. *A42B 1/008* (2013.01); *A42B 3/286* (2013.01); *A61M 16/107* (2014.02); *A62B 18/003* (2013.01); *A62B 18/04* (2013.01)

(58) Field of Classification Search
CPC ......... A42B 1/008; A42B 3/286; A62B 18/04; A62B 18/003; A61M 16/107
See application file for complete search history.

(56) References Cited

U.S. PATENT DOCUMENTS

| | | | |
|---|---|---|---|
| 2,032,101 | A | 2/1936 | Sullivan |
| 2,333,054 | A | 10/1943 | Sullivan |
| 2,688,962 | A | 9/1954 | Summers |
| 3,813,696 | A | 6/1974 | Yeager |
| 3,881,478 | A | 5/1975 | Rosendahl et al. |
| 3,925,821 | A | 12/1975 | Lewicki |
| 4,227,520 | A | 10/1980 | Lord |

(Continued)

FOREIGN PATENT DOCUMENTS

| | | |
|---|---|---|
| DE | 3306691 | 9/1984 |
| DE | 3306692 | 9/1984 |

OTHER PUBLICATIONS

Jan. 11, 2016 PCT Preliminary Examination Report (Serial No. PCT/US14/67157)—Our Matter 5214.

(Continued)

*Primary Examiner* — Khaled Annis
(74) *Attorney, Agent, or Firm* — Tysver Beck Evans

(57) ABSTRACT

A hard hat with air flow system includes a hard hat with an air flow passage for passing air through the hard hat and out exits ports at the front of the hat to provide a shield of air downward across the face of a user. The system includes an air filtration system, a blower assembly for drawing air through the air filter and pushing the filtered air into the air flow passage of the hard hat, and a power supply for powering the blower. The filtration system, blower assembly and power supply being supported on a harness such as a belt or backpack, external from the hard hat.

13 Claims, 12 Drawing Sheets

(56) References Cited

U.S. PATENT DOCUMENTS

| | | | |
|---|---|---|---|
| 4,803,979 A | 2/1989 | Fischer | |
| 5,050,240 A | 9/1991 | Sayre | |
| 5,283,914 A | 2/1994 | James | |
| 5,577,495 A | 11/1996 | Murphy | |
| 5,592,936 A | 1/1997 | Thomas, Jr. et al. | |
| 6,081,929 A | 7/2000 | Rothrock et al. | |
| 6,513,168 B2 | 2/2003 | Paris et al. | |
| 6,810,532 B2* | 11/2004 | Wang Lee | A42B 3/281 128/200.28 |
| 6,904,616 B1 | 6/2005 | Maki et al. | |
| 6,973,676 B1* | 12/2005 | Simpson | A42B 3/288 128/201.24 |
| 6,990,691 B2 | 1/2006 | Klotz et al. | |
| 7,036,502 B2 | 5/2006 | Manne | |
| 7,114,194 B2 | 10/2006 | English | |
| 8,590,062 B2 | 11/2013 | Gupta | |
| 10,299,525 B1* | 5/2019 | Buckman | A42B 1/008 |
| 2002/0073994 A1* | 6/2002 | Patel | A62B 9/02 128/201.17 |
| 2003/0182711 A1 | 10/2003 | Klotz | |
| 2005/0114986 A1 | 6/2005 | Hobart | |
| 2006/0053528 A1 | 3/2006 | English | |
| 2007/0044800 A1 | 3/2007 | Church et al. | |
| 2007/0089221 A1 | 4/2007 | Manzella, Jr. et al. | |
| 2007/0094768 A1 | 5/2007 | Moudgill | |
| 2007/0094769 A1 | 5/2007 | Lakes et al. | |
| 2007/0163588 A1* | 7/2007 | Hebrank | A61L 9/16 128/204.18 |
| 2009/0055987 A1 | 3/2009 | Becker et al. | |
| 2009/0210989 A1 | 8/2009 | Becker et al. | |
| 2009/0250060 A1 | 10/2009 | Hacke | |
| 2010/0294270 A1 | 11/2010 | Curran et al. | |
| 2012/0051904 A1* | 3/2012 | Hagen | A62B 18/006 415/224 |
| 2012/0167282 A1 | 7/2012 | Fleming et al. | |
| 2013/0014752 A1* | 1/2013 | Ausen | A62B 7/10 12/201.25 |
| 2013/0118487 A1* | 5/2013 | Huh | A62B 9/006 128/202.22 |
| 2013/0263364 A1 | 10/2013 | Green | |
| 2013/0306072 A1* | 11/2013 | Moir | A61M 16/0066 128/204.18 |
| 2014/0026300 A1* | 1/2014 | Silveira | A61F 9/068 2/431 |
| 2014/0166001 A1* | 6/2014 | Kooken | A62B 7/10 12/201.25 |
| 2015/0174435 A1* | 6/2015 | Jones | A62B 7/10 128/202.13 |
| 2015/0296917 A1* | 10/2015 | Perusse | A42B 3/286 2/15 |
| 2017/0136268 A1* | 5/2017 | Boffey | A62B 9/006 |
| 2019/0175961 A1* | 6/2019 | Awiszus | A42B 3/0453 |

OTHER PUBLICATIONS

Oct. 2, 2017 USPTO Office Action (U.S. Appl. No. 15/369,205)—Our Matter 5497.
Oct. 23, 2015 PCT Preliminary Examination Report (Serial No. PCT/US14/67157)—Our Matter 5214.
Mar. 3, 2015 PCT Search Report (Serial No. PCT/US14/67157)—Our Matter 5214.
3M Respiratory Products, http://www.westernsafety.com/3m/3mrespiratorypg4.html, p. 1-17, May 21, 2013.
Jun. 23, 2016 USPTO Office Action (U.S. Appl. No. 14/551,854)—Our Matter 5210.

* cited by examiner

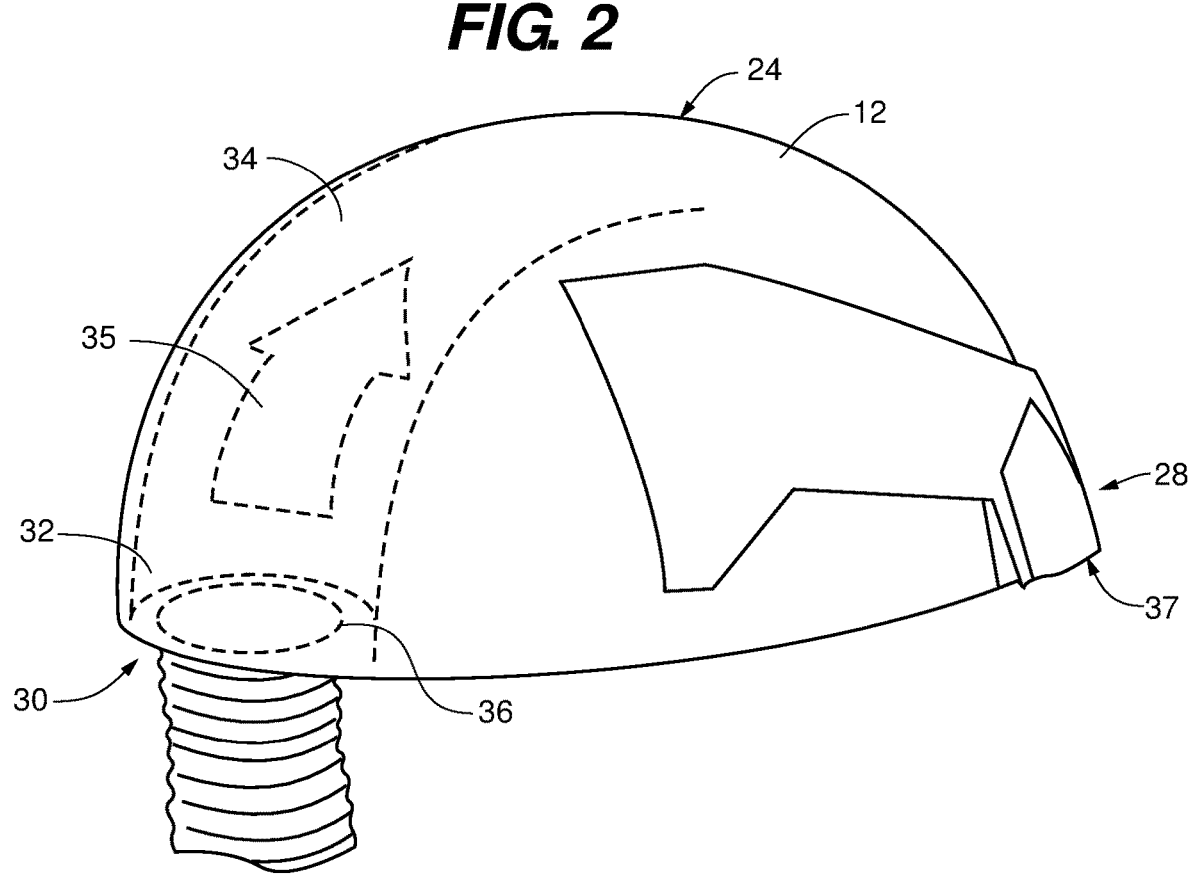

HARD HAT WITH FILTERED, BATTERY-OPERATED AIR FLOW SYSTEM AND METHOD

FIELD OF THE INVENTION

The present application relates to the field of hard hats such as are used in the construction and painting industries. More particularly, the application relates to a hard hat with an external blower/fan and air filtration system that provides filtered air flowing over a user's face to keep eyes and/or eyewear relatively free of paint and dirt contaminants.

SUMMARY

A hard hat having an air flow system which draws air through a filter cartridge via a blower and passes the filtered air through an air passage in a hard hat is known. Examples of such hard hats and systems are described in U.S. Pat. No. 9,510,632; U.S. published App. No. 2014/352,657; U.S. application Ser. No. 15/369,205 and U.S. application Ser. No. 15/656,557 the entire contents of each being incorporated herein by reference. These systems produce a curtain of air in front of the wearer's face. Such hard hats however, require that all the necessary components of the air flow system, including a fan or blower (hereinafter collectively referred to as a blower), and the air filter system are all contained within the confines of the hard hat. Such an assemblage of parts within the hard hat may result in a hat that is potentially bulkier and/or heavier than may be optimal.

Thus, a need continues to exist to provide a hard hat having such an air flow system incorporated therein, but which does not insist in having all of the air flow components contained within the confines of the hat interior.

Embodiments disclosed herein address this need and provide a hard hat and air flow system wherein the blower, its power supply, and the air filter components of the system are mounted externally from the hard hat on a harness such as a belt or backpack worn by the wearer of the hard hat. In the various embodiments disclosed herein, the blower and air filter are connected to one another and to the air intake of the hard hat by air flow tubing.

BRIEF DESCRIPTION OF THE DRAWINGS

FIG. 2 is a rear side perspective view of an embodiment of the hard hat utilized with the system shown in FIG. 1a, wherein a partial depiction of the internal air flow pathway is illustrated.

FIG. 6 is a close-up view of an alternative arrangement of the belt mounted filter assembly, blower housing, and connective air flow tubing of the system shown in FIG. 1a.

DETAILED DESCRIPTION

Figure 1A:
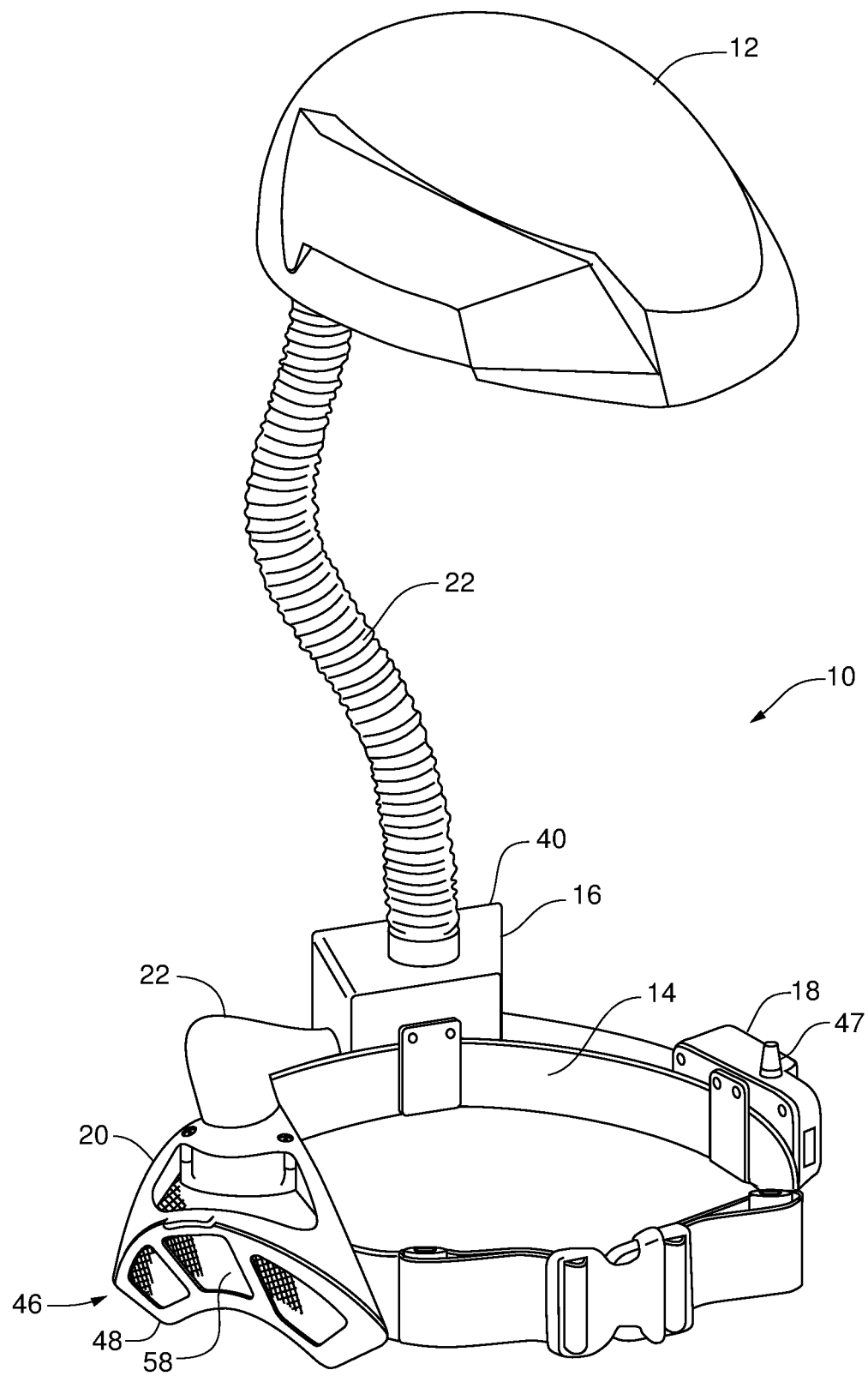
FIG. 1a is a perspective view of an embodiment of the present system wherein the system includes a support belt.

As mentioned above, embodiments of the present disclosure are provided in the form of hard hat and air flow system 10, such as is illustrated in FIG. 1a, and which includes a hard hat 12, as well has a belt 14, which supports a blower assembly 16, power supply 18 and an air filter assembly 20. Each of the aforementioned components engaged to and supported by the belt may be repositioned or adjusted relative to one another along the length of the belt as may be desired by the user.

Figure 1B:
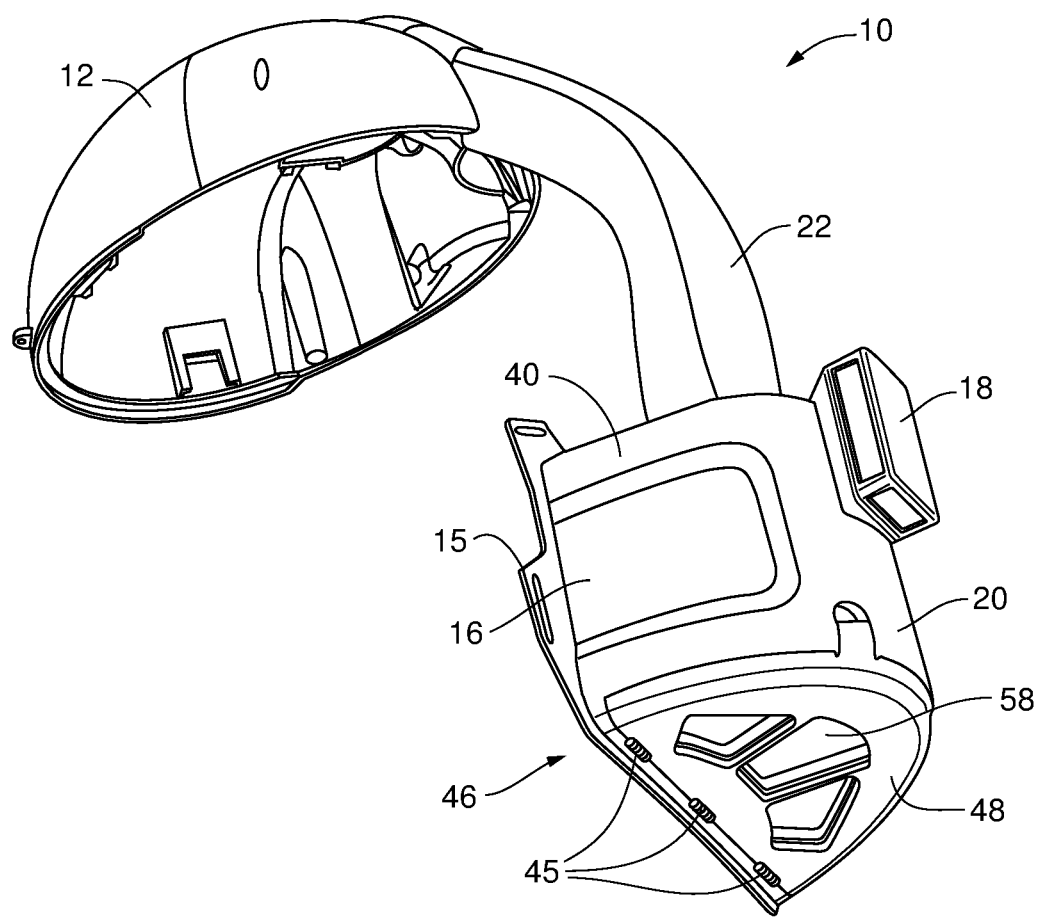
FIG. 1b is a perspective view of an embodiment of the present system wherein the system includes a backpack.

In at least one embodiment, an example of which is shown in FIG. 1b, the blower assembly 16, power supply 18 an air filter assembly 20 are incorporated into a backpack 15 (shoulder and/or waist securement straps not shown).

Flexible air flow conduit or tubing 22 connects the hat 12, blower assembly 16 and air filter assembly 20 so that air may pass between these components in an uninterrupted pathway.

The hard hat 12 may be of any style or configuration and may be of uniform or customized size, such that a variety of individual wearers or users may wear the hard hat 12 for prolonged periods of time, and in a variety of environments.

In its most basic form the hard hat 12 includes a shell 24, a bill or brim (hereinafter "bill") 26 at the front or face 28 of the shell 24 and a back 30 of the shell 24 where air flow tubing 22 is attached to and in fluid engagement with the internal structure 32 (see FIG. 2 and detailed discussion below) of the hard hat 12 that forms the air flow pathway 34 of the hard hat such as in the manner shown in FIG. 2.

As FIG. 2 makes clear, in at least one embodiment, the air flow pathway 34 of the hat 12 is defined by the internal structure 32 of the hat 12 which underlies the shell 24. The air flow pathway 34 extends from the conduit or tubing engagement or air flow inlet port 36 at the back of the hat 12 and extends up and over the wearer's head to the front 28 of the hat 12 where the internal structure 32 defines a plurality of exit ports 37 (see FIGS. 8-11) through which air (represented by arrow 35b), passing through the air flow pathway 34, exits the hat 12 and pass in front of the wearer's face with sufficient velocity to repel particles of paint, dust, fumes and similar industrial contaminants.

Figure 3:
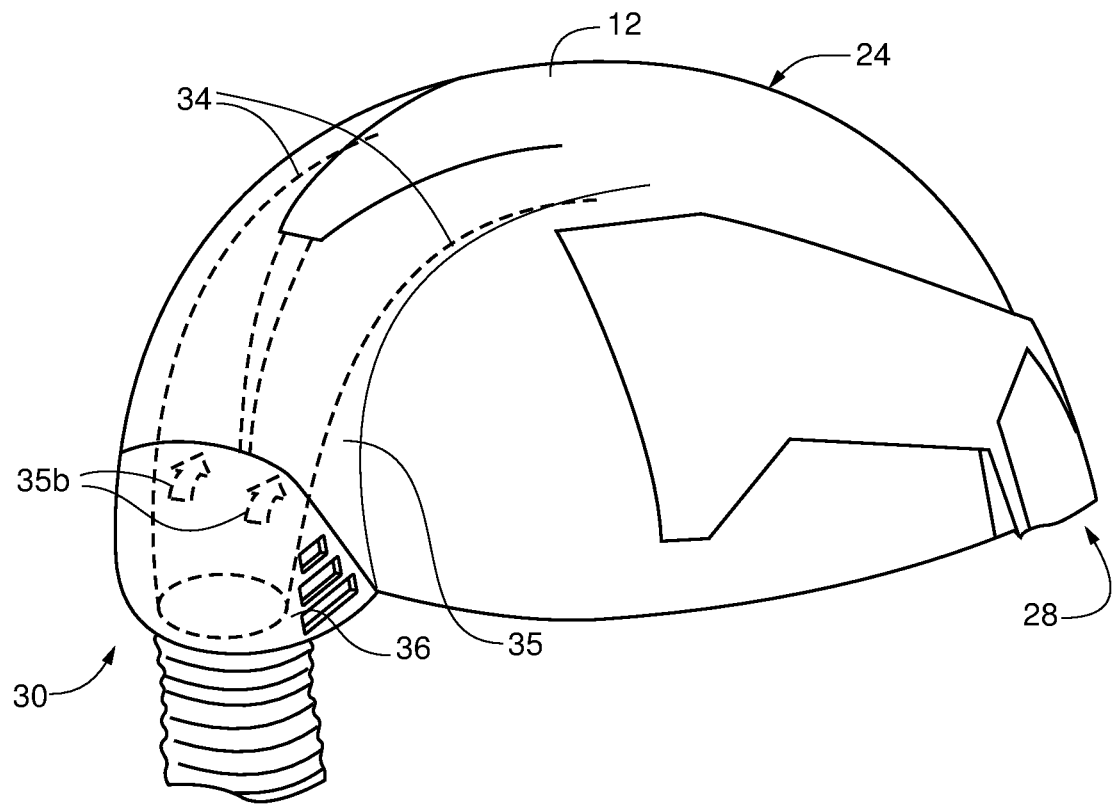
FIG. 3 is a rear side perspective view of an alternative embodiment of the hard hat shown in FIG. 2.

In an alternative embodiment, such as may be seen in FIG. 3, the tubing engagement or air inlet port 36 and the air flow pathway 34 are formed by the shell 24 or is external to the shell 24 (a protrusion of the shell 24) at the back 30 of the hat 12. The air flow pathway 34 functions identically to that of the embodiment shown in FIG. 2, but for the "internal structure" being an "external" structure 38 in that it is not contained in the hard hat interior. This distinction between a hat 12 having an internal structure that defines the pathway 34 and one having an external structure 38 which defines the pathway 34 is clearly illustrated by comparing the embodiments of FIG. 2 and FIG. 3.

Returning to FIGS. 1a and 1b, we now focus on the components of the system 10, which are configured to filter and draw/push air to the hard hat 12 in the manner discussed above. In the embodiment shown, the system 10 includes a blower assembly 16 which includes a blower housing 40 and a blower 42 mounted therein, in the manner shown in FIG. 4. Blower 42 is electronically coupled to and powered by a power supply 18. Power supply 18 may be a battery, batteries or other power supply mechanism. As illustrated in FIG. 1a, in some embodiments the power supply 18 is a battery pack that is mounted to the belt 14 and in electrical communication with the blower 42 via wires or other electrical communication mechanisms. In some embodiments, such as is shown in FIG. 1b, the power supply 18 is directly engaged to the blower housing 40. This engagement both mechanically couples the power supply 18 to the housing 40 but also provides a direct electrical linkage between the power supply and blower 42.

Figure 5:
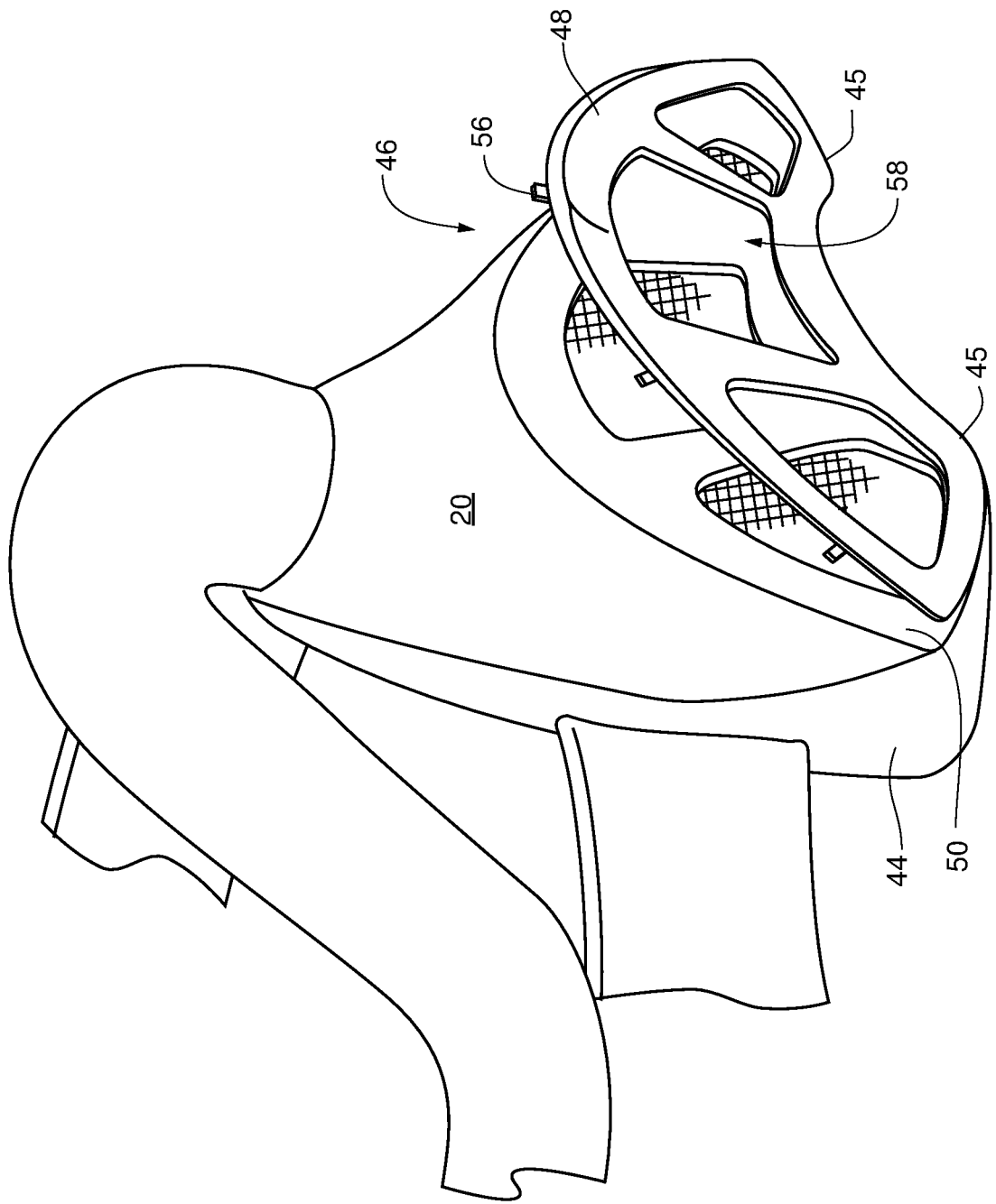
FIG. 5 is a detailed perspective view of the filter assembly shown in FIG. 1a, wherein the filter cartridge is shown adjacent to the filter basket which is in the open position relative to the filter housing.

The blower housing 40 is in fluid communication with the housing 44 of a filter assembly 20 via air flow tubing 22. Engaged to the filter housing 44 is a filtering system 46 (best shown in FIG. 5), which includes a support cage or basket 48 and a filter cartridge 50. In the embodiment shown in FIG. 1a the filtering basket 48 is an external cover pivotally connected to the filter housing 44 at hinges 45, so as to allow the filtering system 46 to be pivotally opened and closed relative to the filter housing 44, in order to allow a user ease of access to the replaceable filter cartridge 50 retained thereunder.

In some embodiments, a single hinge 45 may be used to secure the system 46 to the housing 44. Likewise, in some embodiments, two or more hinges 45 may be utilized. The system 46 may be snap fit or otherwise be mechanically and removeably engageable to the housing 44 when in the closed or operational position shown in FIG. 1a.

In embodiments wherein the system includes a backpack 15, such as illustrated in FIG. 1b, the blower 42 is retained within a blower housing 40 that is immediately adjacent to the filter housing 44 to the extent that the housings 40 and 44 are shared such as in the manner illustrated. In such an embodiment cartridge 50 is retained by the basket 48 at the bottom surface of the backpack 15.

Figure 4:
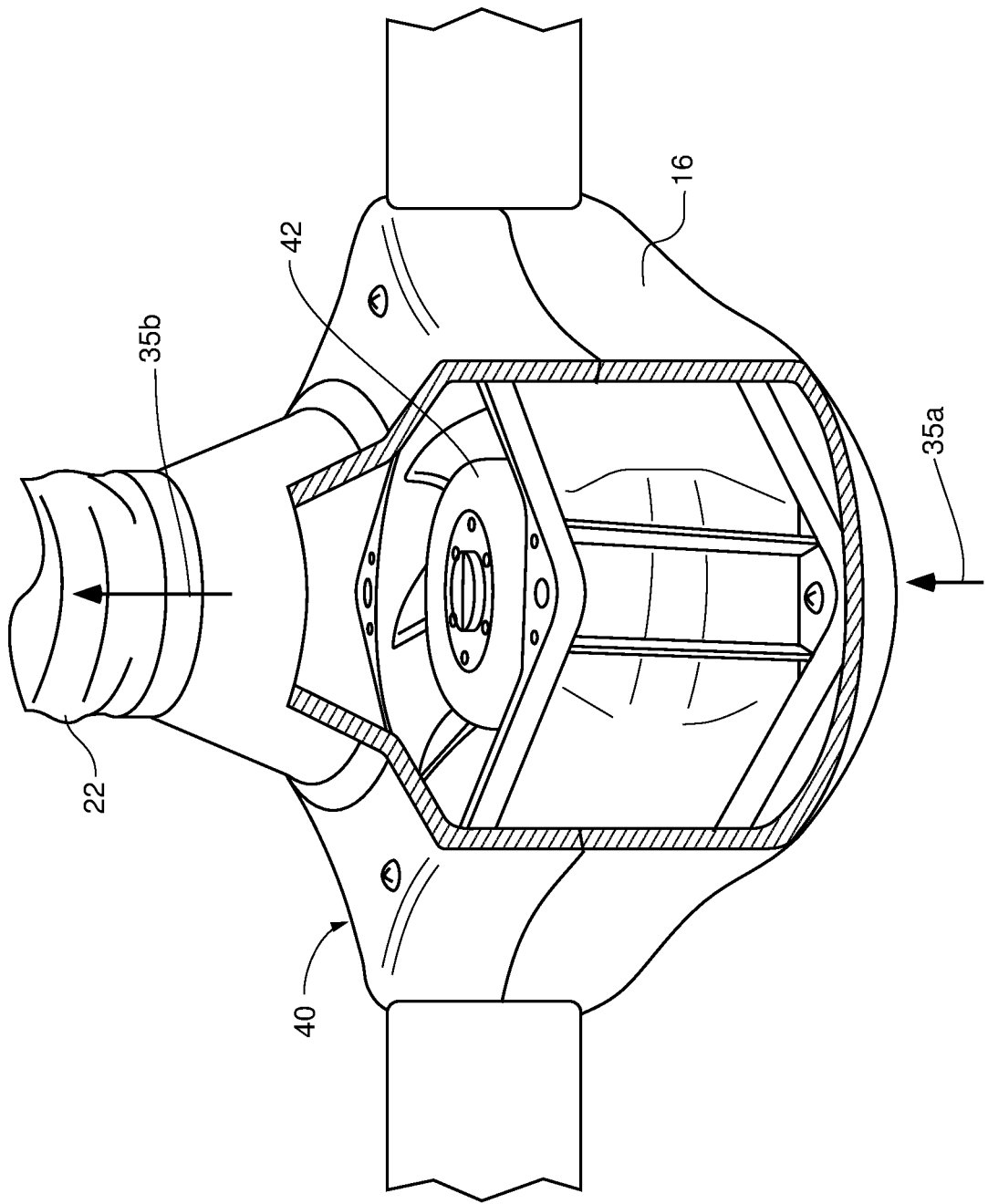
FIG. 4 is a detailed perspective view of the blower housing shown in FIGS. 1a and 1b, wherein the housing is shown partially cut away to reveal the position of the blower therein and the manner in which the blower draws in and expels air.

Functionally, when the blower 42, such as is shown in FIG. 4, is activated via control 47, the blower 42 draws air (represented by arrow 35a in FIG. 4) through the air filtering system 46, through the filter housing 44 and into air flow tubing 22 and into the blower housing 40. The blower 42 then pushes air (represented by arrow 35b in FIG. 4) out of the blower housing 40, upward and into air flow tubing 22 and on to the air flow pathway 34 of the hard hat 12 such as is shown in FIGS. 1a, 1b, 2 and 3.

Figure 6:
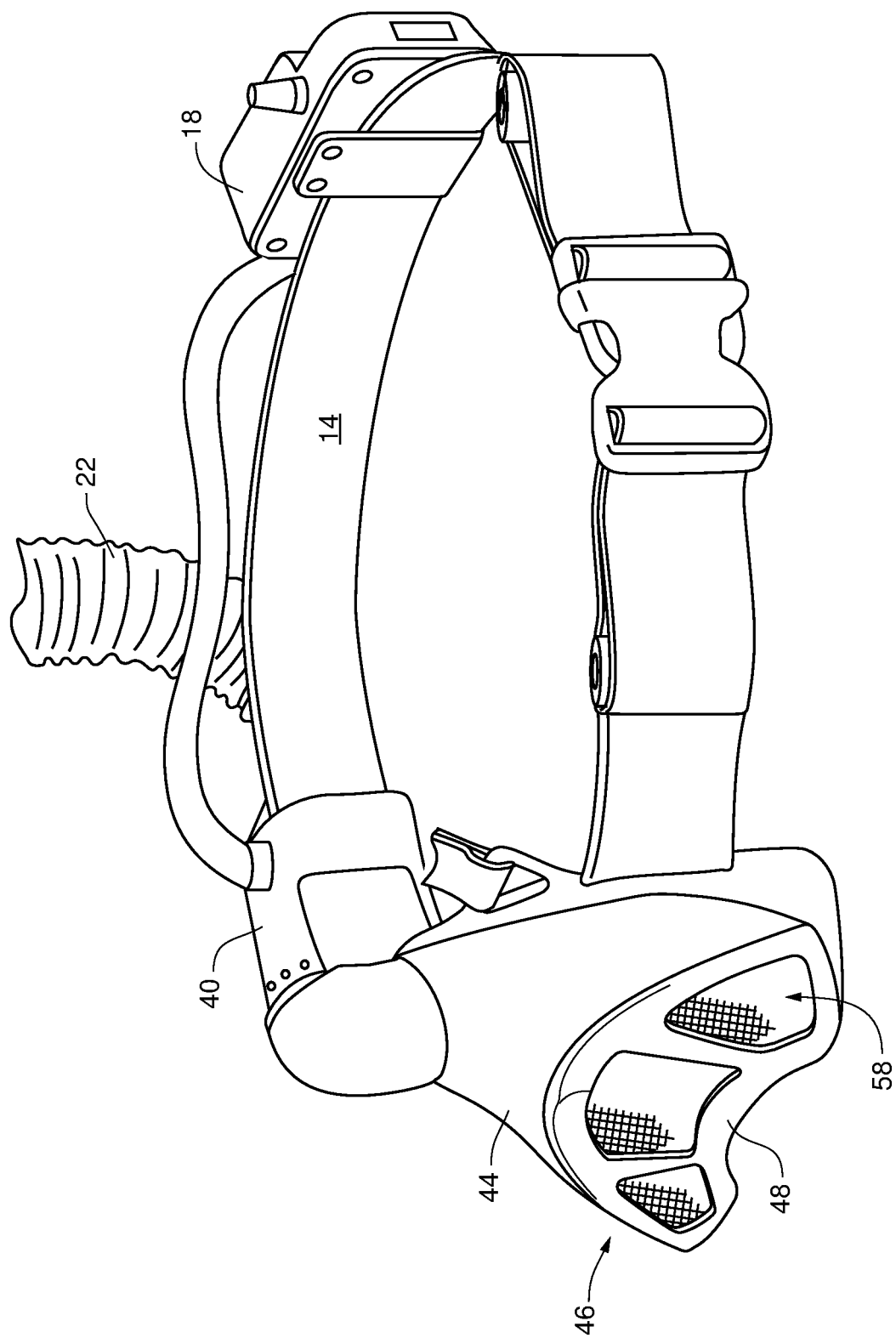

An alternative embodiment to that which is shown in FIG. 1a, is shown in FIG. 6. In this embodiment, the blower housing 40 is immediately adjacent to or even a contiguous portion of the filter housing 44; much in the same manner as in the backpack embodiment discussed above and shown in FIG. 1b. In this embodiment, potentially extraneous tubing 22 connecting the housings 40 and 44 is eliminated.

Figure 7:
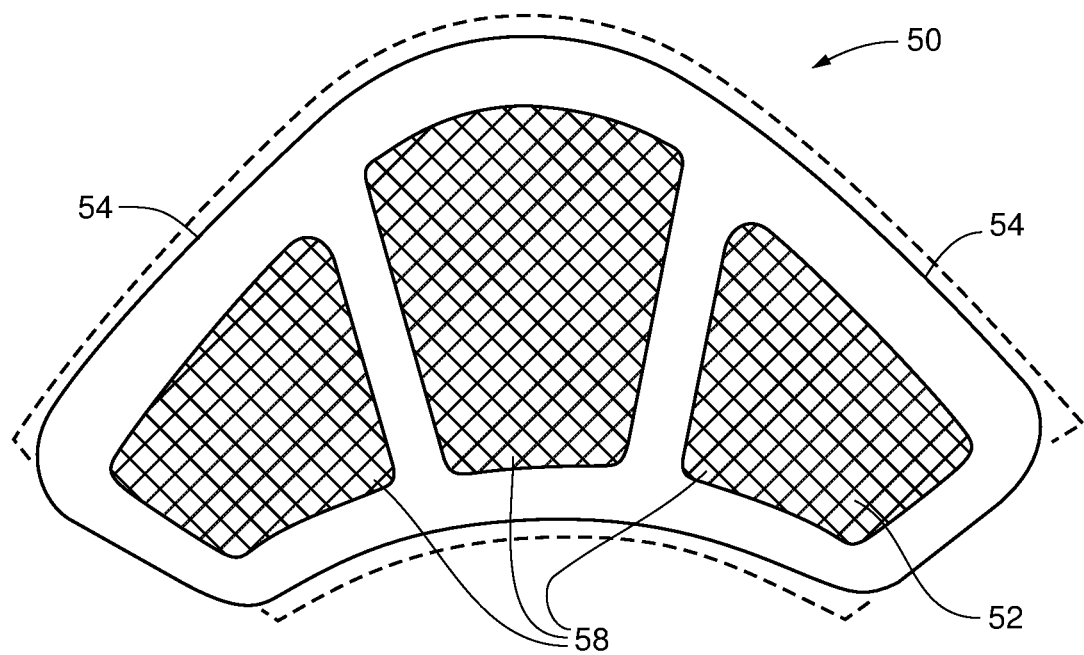
FIG. 7 flat view of the filter cartridge shown in FIG. 6 to better illustrate its geometry and construction.

Turning now to the filter cartridge 50 and its construction, an embodiment of the filter cartridge 50 is shown in FIG. 7. As previously mentioned, the filtering system 46 includes a cage or basket 48 to which a replaceable filter cartridge 50 is engaged to when positioned within the filter housing 44. The basket 48 is itself the part of the system 46 that is pivotally or otherwise mechanically engaged to the filter housing 44 as previously described above and shown in FIGS. 1a, 1b and 5.

As is shown in FIG. 7 the cartridge 50 a filter medium 52 and supporting frame 54. Filter medium 52 may be any sort of filtration material suitable for the removal of particulate matter suspended in air being drawn therethrough. As air is intended to be drawn and pass through the filter medium 52, the porosity of the medium must be appropriate to that task. However, depending on the intended environment of use the porosity may be varied to allow filtration of suspended particles of solid or liquid; and in some embodiments even some gasses (fumes). For example, when the hard hat 12, such as is shown in FIG. 1, is intended for use in conditions involving paint or drywall cutting, the medium 52 may be of a finer type of filtration material than might be used in conditions where larger suspended particles are more likely to be present (saw dust present at a building site, etc.). Some examples of suitable material that may be included in the medium 52 includes but is not limited to: Tyvek, open celled foam, and/or other materials suitable for their use in air filtration systems. Details and additional embodiments of the cartridge 50 are provided in parent U.S. patent application Ser. No. 15/656,557, filed Jul. 21, 2017, the entire contents of which are incorporated herein by reference.

Medium 52 is engaged to support frame 54 through the use of adhesives, mechanical engagement (hook and loop style complementary surfaces for example), or even merely by sandwiching the medium 52 between the frame 54 and an adjacent structure such as the housing 44 or basket 48. In some embodiments, the cartridge 50 or its individual components (medium 52 and/or frame 54) interact with protrusions or tabs 56 (see FIG. 5) on the basket 48 to removeably engage the cartridge 50 to the basket 48 to form the filtration system 46.

Frame 54 (and basket 48 in the closed state such as is shown in FIGS. 1a and 1b) define air flow openings 58 which allows for air to be drawn therethrough to pass through the adjacent medium 52 and into fan 42 through the air-intake 44. The shape of the housing 44 and orientation of the basket 48 relative thereto may be varied, such that the basket 48 (and underlying filter cartridge 50 visible in FIG. 5) may be oriented to draw air from any direction relative to the housing 44 and the supporting belt 14 (or backpack 15 in the embodiment shown in FIG. 1b) when the blower is activated. In FIG. 1a for example the basket is oriented such that it will pull air into the openings 58 from a direction adjacent to and below that of the housing 44 and belt 14. Similarly, in the embodiment shown in FIG. 1b, the back pack 15 is configured such that air will be drawn into the openings 58 from a direction directly beneath the backpack 15 and housing 44. The housing and 444 and basket 48 may be configured such that air may be drawn through the openings 58 from any direction desired.

Cartridge 50 is shown disengaged from the basket 22 in FIG. The cartridge 50 is a distinct and separable element of the air filter system 46 that is designed to be removable and replaceable. As has been repeatedly discussed, typically the cartridge includes a cage or frame 48 with a filter medium 52 engaged thereto. If desired, filter housing 44 may include multiple cartridges 50 or additional filter medium positioned within the housing 44, adjacent to the cartridge 50.

In the preferred embodiment, the cartridge 50 includes a frame or cage 54 and a medium 52 secured thereto by adhesive, mechanical or other form of engagement. The entire cartridge 50 may be removed from the basket 48 to be disposed of and then readily replaced with a new cartridge 50. In some embodiments, the cartridge 50 may be rinsed or otherwise cleaned for repeated use.

As indicated above, the cartridge 50 must be configured to ensure that air passing the openings 58 of the basket 48 is passed through the medium 52 and thusly filtered before passing into the filter housing 44 and into the remainder of the air flow components of the system 10. One way that such proper alignment is ensured is by providing the cartridge 50, and thus the cage 54 and medium 52 with a shape the conforms to that of the basket 48 (see FIGS. 1*a*, 1*b* and 5-6).

In the various embodiments shown, the cartridge 50 (and its component cage 54 and medium 52) has a chevron or boomerang-like shape. This shape corresponds to the shape of the retaining cover or basket 48 which engages the cartridge 50 and hold it in position within the housing 44, such that air flow is forced exclusively through openings 58 of the basket 48 and frame 54.

In the embodiment shown, frame 54 includes three openings 58 to allow air to pass through the medium 52. Frame 54 and basket 48 may be constructed and arranged to allow for any number of openings through which air is forced to pass through medium 52.

The unique size and shape of the filtration system 46 and the manner in which it engages the filter housing 44, ensures that when positioned within the housing 44, the openings 56 of the frame and basket overlap and thereby ensuring that air flowing through openings 56 will pass through the filter medium 52 positioned therebetween.

Having filtered particulates from the air 35 passing through the medium 52, air 35*a* is drawn from the filter assembly 20 and into the blower housing 40 such as in the manner shown in FIGS. 1*a* and 1*b* (see also FIG. 4). The blower 42, then pushes the air 35*b* upward through tubing 22 toward the hard hat 12. Air passes into the air flow pathway 34 of the hard hat 12 starting at the engagement port 36 as is illustrated in FIGS. 2 and 3.

Regardless of the location of the pathway 34 or its definition by an internal structure 32 (see FIG. 2) or an external structure 38 (see FIG. 3) the actual functionality of the pathway 34 is the same: to pass the air 35*b* entering the pathway 34 at the engagement port 36 at the back 30 of the hard hat 12, up and over the head of the wearer through the pathway 34 and out the exit ports 37 positioned at the front 28 of the hard hat 12, such that the air flow passes in front of the wearer's face with sufficient velocity to repel particles of paint, dust, fumes and similar industrial contaminants. An embodiment illustrating an internal structure 32 defined pathway 34 is shown in FIGS. 8-9, and an external structure 38 defined pathway 34 is shown in FIG. 10.

In the case of an internal structure 32, the pathway 34 underlies the shell 24 (shown in FIG. 2). The internal structure 32 has a length that extends from the engagement port 36 at the back 30 of the hard hat 12 to the front 28 of the hard hat 12. The framework 32 may be made of any suitable material for containing and directing the flow of air 35*b* provided by fan/blower 42. Such materials may include light weight plastic, polymers, rubber (natural or synthetic) or even reinforced cardstock (cardboard) or other easily replaced material. The interior framework 32 may be formed separately from, and then attached to the shell 12, or the shell 12 and interior framework 32 may be formed as a unitary entity.

Figure 8:
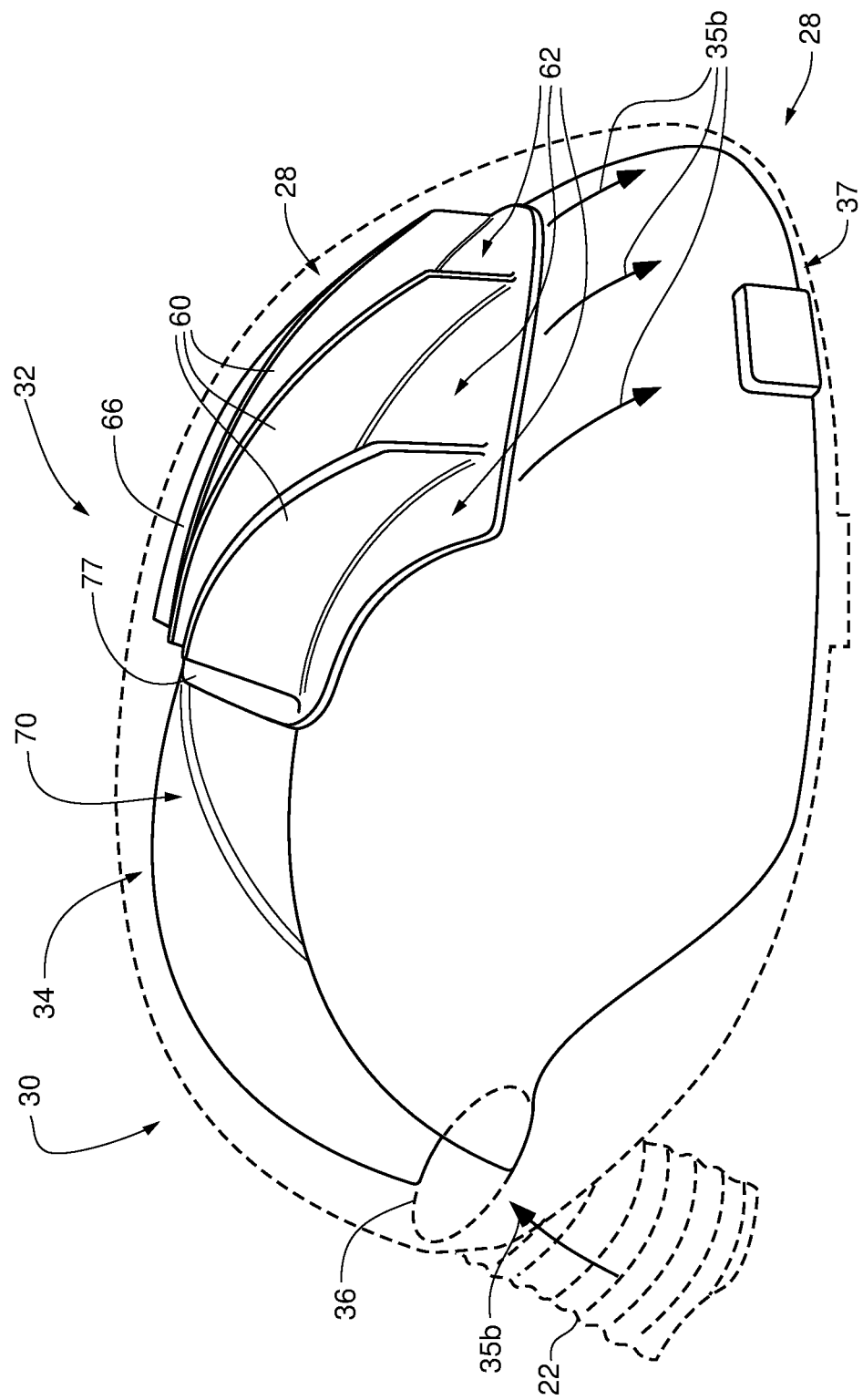
FIG. 8 is a front side perspective view of the internal structure of the hard hat shown in FIG. 2 which defines the air flow path through the interior of the hard hat.
Figure 9:
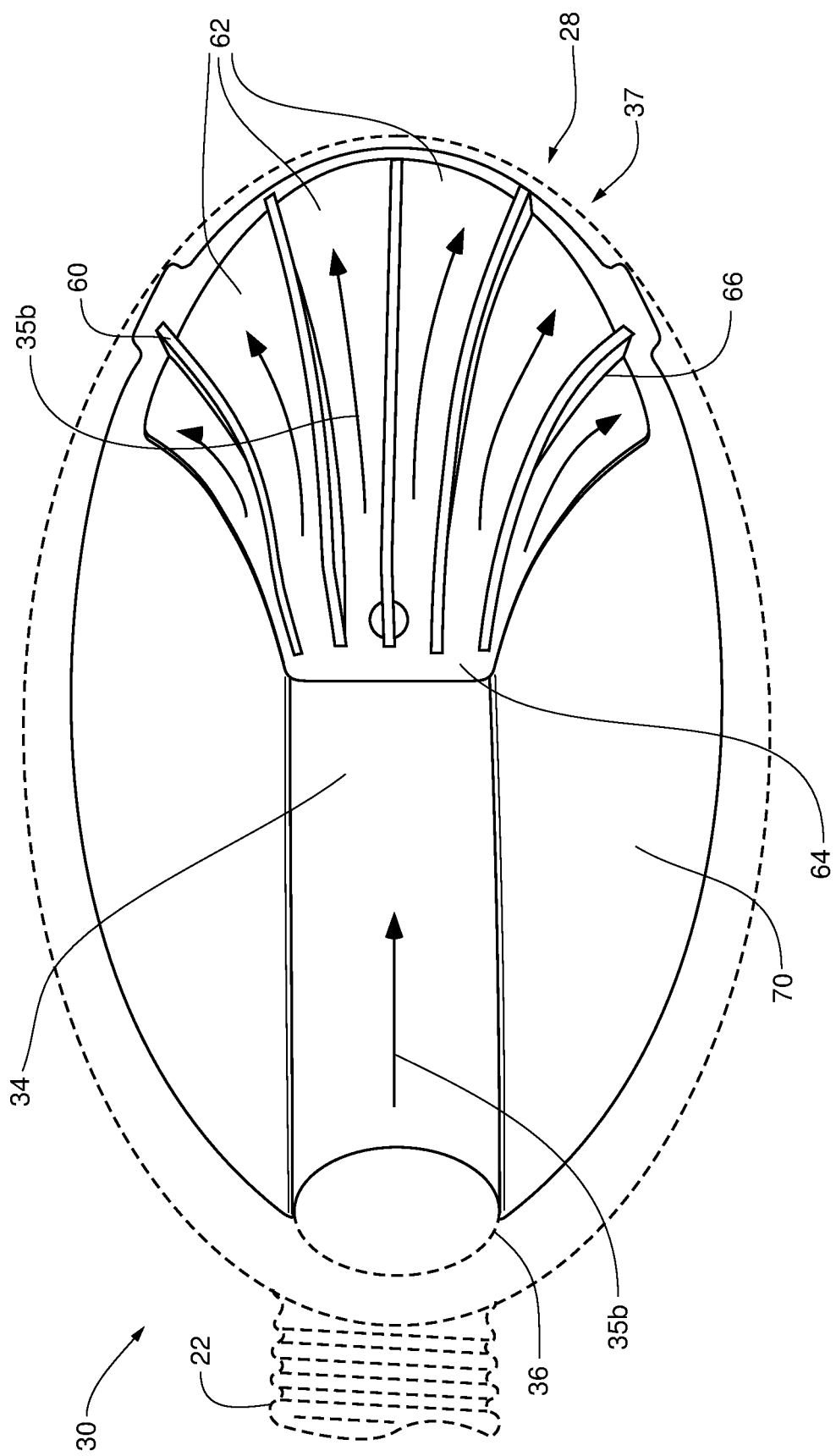
FIG. 9 is a top down view of the hard hat internal structure shown in FIG. 8.
Figure 10:
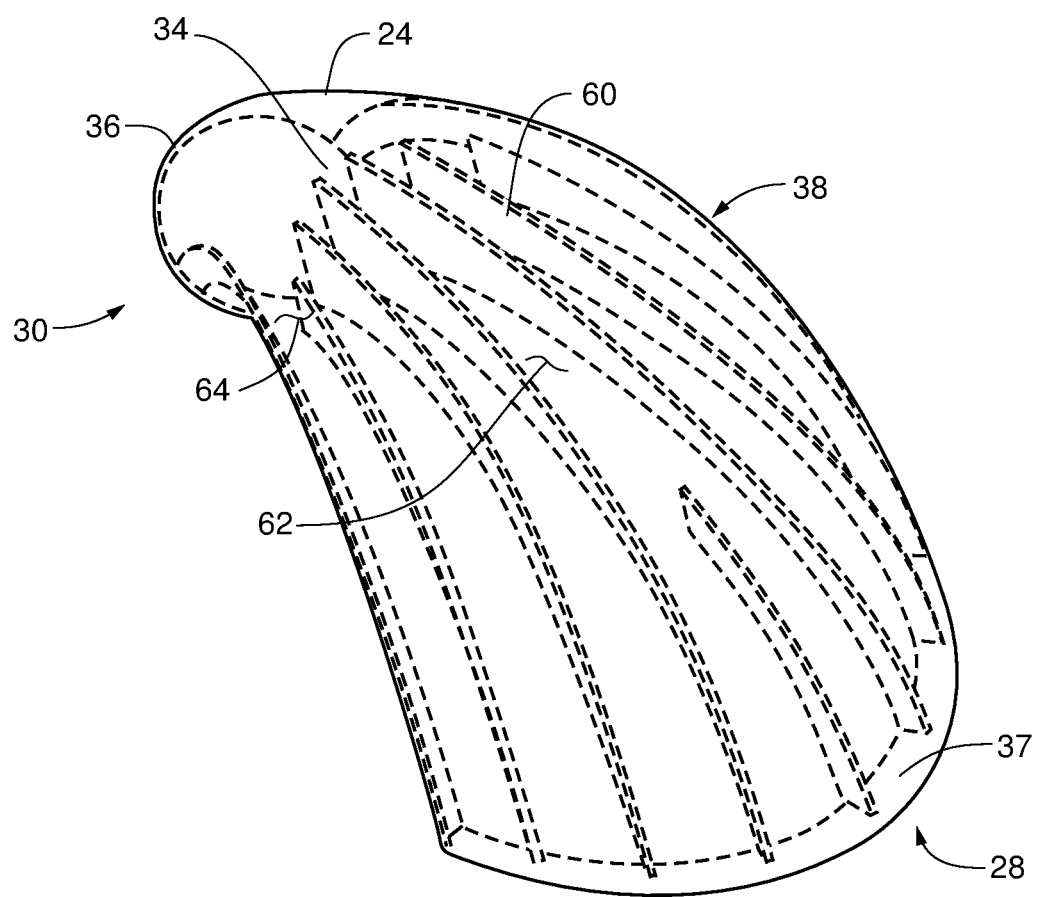
FIG. 10 is a perspective view of the external structure of the hard hat shown in FIG. 3 which defines the air flow path adjacent to and/or through the shell of the hard hat.
Figure 11:
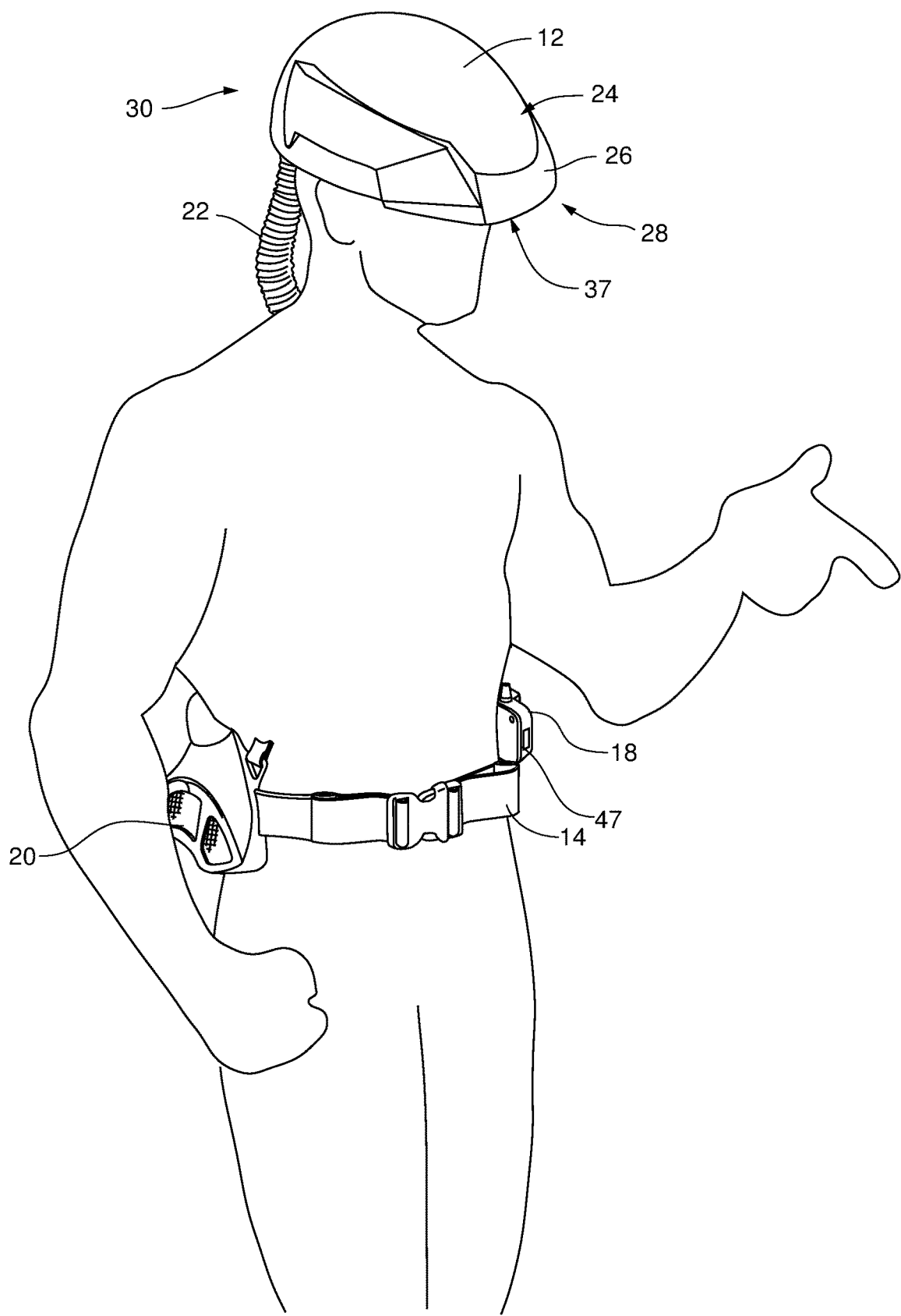
FIG. 11 is a perspective view of the embodiment shown in FIG. 1a depicted being worn by an end user.

As is shown in FIG. 8-9, air 35*b* passes through the blower and into an air passage inlet at engagement port 36. The air passage inlet is simply where the air passes from the tubing 22 and into the hat internal structure 32. The air flow pathway 34 defined by the internal structure 32 is therefore in fluid communication with the blower 42 via the tubing 22 such as in the manner shown in FIGS. 1*a*, 1*b* and 4.

This air flow pathway 34 is divided by the presence of a plurality of walls 60 that form air directing channels 62 therebetween. In some embodiments, the walls 60 form channels 62 that expand in width along their length, such that a channel 62 may be wider at the exit port 37, toward the front 28 of the hard hat 12, and narrower at the inlet 64 such as in the manner shown in FIG. 9.

The internal framework 32 may be a single molded plastic (or other material) structure containing the walls 60. Alternatively, the internal framework 32 is a two piece (or more) structure including an insert 66 that defines the walls 60 and the predominant air directing channels 62.

Walls 60 may extend the entire length of the framework 32 or only partially along that length such as in the manner shown in FIGS. 8-9. In these figures, the walls 60 begin relatively far along the air flow passage 34 of the hat. This leaves an un-walled cavity 70 in the air flow passage 34 in which the air exiting the tubing 22 first enters. The lack of walls ensures a relatively even pressure of air within this cavity, helping to equalize the air flow that passes through each of the channels 62 formed by the walls 60. The entire air flow path, consisting of the unwalled cavity 70 and the channels 62, extend from the tubing engagement port 36 over the head of the user and are in fluid communication with the exit ports 37 at the front of the hard hat 12 (see FIGS. 1*a*, 1*b* and FIG. 10). Air 35*b* is pushed into the un-walled cavity 70 and into the channels 62 by the previously described blower 42 (see FIG. 4), whereupon it exits the channels 62 through exit ports 37 at the front 28 of the hard hat 12. The air 35*b* exiting the exit ports 37 forms the aforementioned stream or "shield" of filtered air 35*b*, which passes in front of the user's eyes or eyewear with sufficient velocity to repel particles of paint, dust, fumes and similar industrial contaminants such as in the manner shown in FIG. 11.

In the embodiment shown in FIG. 10 a portion of the hard hat 12 which defines an air flow pathway 34 via an external structure 38 such as has been previously described and shown in FIG. 3 is shown in detail. As with the hat having an internal structure 32, the exterior structure 38 likewise provides for an air flow pathway 34 that is divided by the presence of a plurality of walls 60 that form air directing channels 62 therebetween. In some embodiments, the walls 60 form channels 62 that expand in width along their length, such that a channel 62 may be wider at the exit port 37 and narrower at its inlet 64 adjacent to the port 36. The primary structural difference between the internal structure 32 and external structure 38 is that the internal structure 32 underlies and is entirely contained within the interior of hard hat 12, whereas the external structure 38 is a protrusion of or lies upon the shell 24 of the hard hat.

The many features and advantages of the invention are apparent from the above description. Numerous modifications and variations will readily occur to those skilled in the art. Since such modifications are possible, the invention is not to be limited to the exact construction and operation illustrated and described. Rather, the present invention should be limited only by the following claims.

What is claimed is:

1. A hard hat and air flow system comprising:
   a) a hard hat, the hard hat having a shell, and an internal structure positioned internally of the shell, the hard hat having a front and a back, the internal structure and shell defining an air flow passage having an air passage inlet port located at the back of the hard hat and a plurality of exit ports located at the front of the hard hat, the internal structure defining a cavity immediately adjacent to the air passage inlet port at the back, and having a plurality of walls that define a plurality of channels that extend from the cavity at the back to the exit ports at the front, each of the channels having a width, the width of each channel is greater at the front than at the back;

b) a blower, the blower contained in a blower housing, the blower housing in fluid communication with the air passage inlet port, the blower housing positioned external of the hard hat;

c) a power supply, the power supply in electrical communication with the blower; and d) an air filtration system, the air filtration system being engaged to a filter housing, the filter housing positioned adjacent to and in fluid communication with the blower housing, the filter housing positioned external to the hard hat, the air filtration system comprising:

i) a retaining basket defining a plurality of basket openings therethrough, the retaining basket being engaged to the filter housing, and ii) a filter cartridge having a filter medium, the filter cartridge being removeably engaged to the retaining basket.

2. The system of claim 1 further comprising a harness; the harness being a belt, backpack and any combination thereof.

3. The system of claim 2 wherein the harness supporting the blower housing, the power supply and the filter housing, and being adjustably engaged to the blower housing, the power supply and the filter housing.

4. The system of claim 2 further comprising air flow tubing, a first section of air flow tubing connecting the air passage inlet port of the hard hat to the blower housing.

5. The system of claim 4 wherein a second section of air flow tubing extends from the blower housing to the filter housing.

6. The system of claim 4 wherein the blower housing and the filter housing are immediately adjacent to one another.

7. The system of claim 1 wherein the retaining basket is pivotally engaged to the filter housing.

8. The system of claim 7, wherein the filter medium has a porosity, the porosity of the filter medium allowing air to be drawn therethrough but which blocks and retains particulate matter therein.

9. The system of claim 8, wherein particulate matter includes liquids and fumes.

10. The system of claim 7, wherein the filter cartridge includes a support frame, the filter medium being engaged to the support frame, the support frame constructed and arrange to be mechanically coupled to the retaining basket.

11. The system of claim 1, wherein air passing through the exit ports forms a stream of air.

12. The system of claim 11, wherein the plurality of exit ports correspond to a position on the hard hat such that air flowing through the plurality of exit ports passes over a face of a wearer of the hard hat with sufficient velocity to repel particles.

13. The system of claim 1, wherein each of the air flow channels has a length and a width, wherein the width increases along the length such that the width of each air flow channel is narrowest at the air flow inlet port and widest at the exit port.

* * * * *